United States Patent
Ruppert et al.

(10) Patent No.: US 10,603,256 B2
(45) Date of Patent: Mar. 31, 2020

(54) OIL/WATER ACTIVE INGREDIENT EMULSION CONTAINING UV FILTER

(71) Applicants: Stephan Ruppert, Hamburg (DE); Claudia Steikert, Hamburg (DE); Alexandra Blohm, Hamburg (DE)

(72) Inventors: Stephan Ruppert, Hamburg (DE); Claudia Steikert, Hamburg (DE); Alexandra Blohm, Hamburg (DE)

(73) Assignee: Beiersdorf AG, Hamburg (DE)

( * ) Notice: Subject to any disclaimer, the term of this patent is extended or adjusted under 35 U.S.C. 154(b) by 137 days.

(21) Appl. No.: 15/359,841

(22) Filed: Nov. 23, 2016

(65) Prior Publication Data
US 2017/0071832 A1 Mar. 16, 2017

Related U.S. Application Data

(62) Division of application No. 13/119,036, filed as application No. PCT/EP2009/006608 on Sep. 11, 2009, now abandoned.

(30) Foreign Application Priority Data

Sep. 16, 2008 (DE) .................. 10 2008 048 328

(51) Int. Cl.
*A61K 8/06* (2006.01)
*A61K 8/49* (2006.01)
*A61K 8/97* (2017.01)
*A61Q 17/04* (2006.01)
*A61Q 17/00* (2006.01)
*A61K 8/35* (2006.01)
*A61K 8/40* (2006.01)

(52) U.S. Cl.
CPC ............... *A61K 8/062* (2013.01); *A61K 8/06* (2013.01); *A61K 8/35* (2013.01); *A61K 8/40* (2013.01); *A61K 8/4966* (2013.01); *A61K 8/97* (2013.01); *A61Q 17/00* (2013.01); *A61Q 17/04* (2013.01); *A61K 2800/592* (2013.01)

(58) Field of Classification Search
CPC ........................... Y10S 514/938; A61Q 17/04
See application file for complete search history.

(56) References Cited

U.S. PATENT DOCUMENTS

| | | | | |
|---|---|---|---|---|
| 5,658,556 | A * | 8/1997 | Gers-Barlag | A61K 8/29 424/401 |
| 2005/0058680 | A1* | 3/2005 | Binder | A61K 8/06 424/401 |
| 2007/0196289 | A1* | 8/2007 | Blatt | A61K 8/35 424/59 |

* cited by examiner

*Primary Examiner* — Gina C Justice
(74) *Attorney, Agent, or Firm* — Abel Schillinger, LLP

(57) ABSTRACT

A cosmetic oil/water emulsion comprising a) 2-ethylhexyl-2-cyano-3,3-diphenylacrylate (INCI: Octocrylene), b) 4-(tert.-butyl)-4'-methoxydibenzoyl methane (INCI: Butyl-methoxydibenzoyl methane), c) licorice extract or licochalcone A.

1 Claim, No Drawings

OIL/WATER ACTIVE INGREDIENT EMULSION CONTAINING UV FILTER

CROSS-REFERENCE TO RELATED APPLICATIONS

The present application is a divisional of U.S. application Ser. No. 13/119,036, the entire disclosure of which is expressly incorporated by reference herein, which is a National Stage entry of PCT/EP2009/006608, filed Sep. 11, 2009, which claims priority under 35 U.S.C. 119 of German Patent Application 10 2008 048 328.1, filed Sep. 16, 2008.

BACKGROUND OF THE INVENTION

1. Field of the Invention

The present invention relates to a cosmetic O/W emulsion comprising
a) 2-ethylhexyl 2-cyano-3,3-diphenylacrylate (INCI: octocrylene),
b) 4-(tert-butyl)-4'-methoxydibenzoylmethane (INCI: butyl methoxydibenzoyl methane),
c) licorice extract or licochalcone A, and the preparation and use thereof.

2. Discussion of Background Information

The skin is the largest organ belonging to humans. It has a large number of vital functions to fulfill, for example the regulation of heat and the barrier function against drying out of the skin and of the entire organism, and as protective equipment against the penetration and absorption of external substances. This barrier function is effected through the epidermis, which as the outermost layer forms the actual protective covering against environmental conditions. With about one tenth of the total thickness, at the same time, it is the thinnest layer of the skin.

The skin is exposed to a large number of physical, chemical and biological stresses. A large number of these stresses lead to temporary or permanent reddening of the skin for various reasons.

So that the skin can fulfill its biological functions, it requires regular cleansing and care. In order to promote regeneration of the skin, to protect it from premature ageing or to avoid irritation, active ingredients are as a rule added to cosmetic skin care products.

The active ingredients employed in skin care include, for example, licorice extracts. The key active ingredient of licorice extract, in particular of *Glycyrrhiza inflata*, in this context is the compound licochalcone A, which has the following structure:

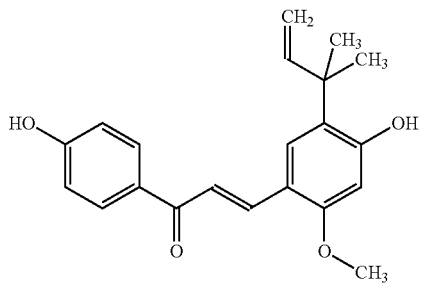 [SMILES: C=CC(C)(C)c1cc(/C=C/C(=O)c2ccc(O)cc2)c(OC)cc1O]

Licochalcone A

Licorice extracts containing licochalcone A are employed in this context in particular to protect against skin irritations, such as reddenings.

A disadvantage of the prior art of cosmetic formulations containing licorice extracts (especially if these extracts contain licochalcone A) is, however, the fact that the extracts and in particular licochalcone A are not particularly storage-stable. If these formulations are stored for a relatively long period of time, and in particular at higher temperatures, degradation of the active ingredient(s) in the formulation occurs and the cosmetic slowly loses effectiveness. This loss in effectiveness occurs to a particularly high degree in O/W emulsions (oil-in-water emulsions).

It was therefore the object of the present invention to eliminate the disadvantages of the prior art and to develop storage-stable or heat-stable cosmetic formulations which contain licorice extracts or licochalcone A.

It was moreover the object of the present invention to develop a formulation which is easy and inexpensive to prepare.

SUMMARY OF THE INVENTION

The object is achieved, surprisingly, by a cosmetic O/W emulsion comprising
a) 2-ethylhexyl 2-cyano-3,3-diphenylacrylate (INCI: octocrylene),
b) 4-(tert-butyl)-4'-methoxydibenzoylmethane (INCI: butyl methoxydibenzoyl methane),
c) licorice extract.

The object is also achieved, surprisingly, by a cosmetic O/W emulsion comprising
a) 2-ethylhexyl 2-cyano-3,3-diphenylacrylate (INCI: octocrylene),
b) 4-(tert-butyl)-4'-methoxydibenzoylmethane (INCI: butyl methoxydibenzoyl methane),
c) licochalcone A.

Surprisingly, the object is achieved in particular by the use of a UV filter combination of
a) 2-ethylhexyl 2-cyano-3,3-diphenylacrylate (INCI: octocrylene),
b) 4-(tert-butyl)-4'-methoxydibenzoylmethane (INCI: butyl methoxydibenzoyl methane)
to increase the storage stability of licochalcone A or licorice extracts in cosmetic O/W emulsions.

The invention relates in this context in particular to the process for the preparation of an O/W emulsion containing licochalcone A and/or licorice extract, characterized in that
a) first the hot aqueous phase is provided,
b) the heated oily phase containing 2-ethylhexyl 2-cyano-3,3-diphenylacrylate, 4-(tert-butyl)-4'-methoxydibenzoylmethane and optionally further oil-soluble UV filters, such as 2,4-bis-{[4-(2-ethyl-hexyloxy)-2-hydroxy]-phenyl}-6-(4-methoxyphenyl)-1,3,5-triazine, is added to the hot aqueous phase,
c) the two phases are subsequently homogenized to give an O/W emulsion,
d) the formulation is cooled,
e) the licorice extract dissolved in ethanol or the licochalcone A dissolved in ethanol is stirred into the emulsion, and the perfume substances and preservatives are subsequently added, and a cosmetic O/W emulsion prepared by this process.

The person skilled in the art indeed knows per se cosmetic formulations with licorice extracts, and in particular with licochalcone A. The German laid-open specifications DE 102 24 387.5, DE 103 52 368.5, DE 103 52 367.7, DE 103 56 723.2, DE 103 56 175.7, DE 103 42 212.9, DE 103 52 369.3, DE 103 56 187.0, DE 103 57 451.4, DE 103 57 452.2, DE 103 56 164.1, DE 103 56 870.0, DE 103 56 869.7 and DE 103 56 866.2 thus describe formulations containing licochalcone A. However, these specifications have not been able to indicate the path to the present invention, since in the recipes disclosed either one of the UV filters required for the invention is missing, or the compositions are present in another base (in particular W/O emulsion).

The licorice extract which is preferred according to the invention originates from the plant *Glycyrrhiza inflata*.

According to the invention, it is furthermore advantageous if the extract is present in the form of an aqueous extract in which
  licochalcone A
  water
  optionally one or more polyols
are present.

According to the invention, it is advantageous if the cosmetic O/W emulsion according to the invention, the use according to the invention or the process according to the invention is characterized in that the formulation or UV filter combination contains as a further constituent 2,4-bis-{[4-(2-ethyl-hexyloxy)-2-hydroxy]-phenyl}-6-(4-methoxyphenyl)-1,3,5-triazine (INCI: aniso triazine).

Where formulations according to the invention or advantageous embodiments etc. are referred to in the context of the present description, this also always relates to the use according to the invention and the preparation process according to the invention or the process product according to the invention.

Embodiments of the present invention which are advantageous according to the invention, characterized in that the formulation contains at least 2.1 wt. %, based on the total weight of the formulation, of 4-(tert-butyl)-4'-methoxydibenzoylmethane.

It is generally preferable according to the invention to employ the constituents according to the invention in the following concentrations:
a) 2-ethylhexyl 2-cyano-3,3-diphenylacrylate (INCI: octocrylene) in a concentration of from 0.1 to 12% by weight, based on the total weight of the formulation.
b) 4-(tert-butyl)-4'-methoxydibenzoylmethane (INCI: butyl methoxydibenzoyl methane) in a concentration of from 0.1 to 8% by weight, based on the total weight of the formulation.
c) licorice extract in a concentration of from 0.001 to 0.05% by weight, based on the total weight of the formulation.
c) licochalcone A in a concentration of from 0.0001 to 0.01% by weight, based on the total weight of the formulation.

2,4-Bis-{[4-(2-ethyl-hexyloxy)-2-hydroxy]-phenyl}-6-(4-methoxyphenyl)-1,3,5-triazine is advantageously employed according to the invention in a concentration of 0.1 from to 5% by weight, based on the total weight of the formulation.

It is advantageous according to the invention if glyceryl stearate citrate, glyceryl stearate SE, stearic acid, polyglyceryl-3 methylglucose distearate, PEG-40 stearate, PEG-100 stearate, potassium cetyl phosphate and/or a mixture of cetearyl alcohol+PEG-40 hydrogenated castor oil+sodium cetearyl sulfate+glyceryl stearate, sodium stearoyl glutamate, sucrose polystearate+hydrogenated polyisobutene polyglyceryl-3 methylglucose distearate triceteareth-4 phosphate is employed as the O/W emulsifier.

Advantageous embodiments according to the invention are also characterized in that the formulation contains one or more UV filters chosen from the group of the compounds phenylene-1,4-bis-(2-benzimidazyl)-3,3'-5,5'-tetrasulfonic acid salts; 2-phenylbenzimidazole-5-sulfonic acid salts; 1,4-di(2-oxo-10-sulfo-3-bornylidenemethyl)-benzene and salts thereof; 4-(2-oxo-3-bornylidenemethyl)benzenesulfonic acid salts; 2-methyl-5-(2-oxo-3-bornylidenemethyl)sulfonic acid salts; 2,2'-methylene-bis-(6-(2H-benzotriazol-2-yl)-4-(1,1,3,3-tetramethylbutyl)-phenol); 2-(2H-benzotriazol-2-yl)-4-methyl-6-[2-methyl-3-[1,3,3,3-tetramethyl-1-[(trimethylsilyl)oxy]disiloxanyl]propyl]-phenol; 3-(4-methylbenzylidene)camphor, 3-benzylidenecamphor, ethylhexyl salicylate; terephthalidenedicamphorsulfonic acid; 4-(dimethylamino)-benzoic acid (2-ethylhexyl) ester, 4-(dimethylamino)benzoic acid amyl ester, 4-methoxybenzalmalonic acid di(2-ethylhexyl) ester, 4-methoxycinnamic acid (2-ethylhexyl) ester; 4-methoxycinnamic acid isoamyl ester; 2-hydroxy-4-methoxybenzophenone, 2-hydroxy-4-methoxy-4'-methylbenzophenone; 2,2'-dihydroxy-4-methoxybenzophenone; 2-(4'-diethylamino-2'-hydroxybenzoyl)-benzoic acid hexyl ester, homomenthyl salicylate; 2-ethylhexyl 2-hydroxybenzoate; dimethicodiethylbenzal malonate; 3-(4-(2,2-bis ethoxycarbonylvinyl)-phenoxy)propenyl)-methoxysiloxane/dimethylsiloxane copolymer, dioctylbutylamidotriazone (INCI: diethylhexyl-butamido triazone); 2,4-bis-[5-1(dimethylpropyl)benzoxazol-2-yl-(4-phenyl)-imino]-6-(2-ethylhexyl)-imino-1,3,5-triazine with the (CAS no. 288254-16-0); 4,4',4"-(1,3,5-triazine-2,4,6-triyltriimino)-tris-benzoic acid tris(2-ethylhexyl ester) (also: 2,4,6-tris-[anilino-(p-carbo-2'-ethyl-1'-hexyloxy)]-1,3,5-triazine (INCI: ethylhexyl triazone); 2,4-bis-(4'-di-neopentylaminobenzalmalonate)-6-(4"-butylaminobenzoate)-s-triazine, titanium dioxide, zinc oxide, trisbiphenyl-triazine 4-dicyanomethylene-2,6-dimethyl-1,4-dihydropyridine N-(ethyloxysulfate ester salt) mono-sodium salt.

It is advantageous according to the invention if the formulation according to the invention is free from p-methylbenzylidenecamphor.

It is preferable according to the invention if the formulation according to the invention contains ethanol. The formulation according to the invention can moreover advantageously contain one or more further compounds with an alcohol function, for example glycerol, 2-methyl-1,3-propanediol, pentane-1,2-diol, hexane-1,2-diol, heptane-1,2-diol, octane-1,2-diol, nonane-1,2-diol, decane-1,2-diol, propanols, propane- and butanediols.

It is advantageous according to the invention if the formulation according to the invention contains one or more antioxidants.

It is preferable according to the invention if the formulation contains one or more compounds chosen from the group of the compounds tocopherol, tocopherol acetate, 2,6-di-tert-butyl-4-methylphenol.

The formulation according to the invention can moreover contain one or more further active ingredients, for example alpha-lipoic acid, folic acid, phytoene, D-biotin, coenzyme Q10, alpha-glucosylrutin, carnitine, carnosine, natural and/or synthetic isoflavonoids, flavonoids, creatine, creatinine, taurine, β-alanine, tocopheryl acetate, dihydroxyacetone, 8-hexadecene-1,16-dicarboxylic acid, glycerylglycose, (2-hydroxyethyl)urea, niacinamide, vitamin A or its derivatives.

It is advantageous according to the invention if the formulation contains one or more polymers. Embodiments which are preferred according to the invention are characterized in that the formulation contains one or more polymers chosen from the group of the compounds acrylate/C10-C30 alkyl acrylate cross polymer, acrylates, carbomers, tapioca starch, xanthan gum.

It is advantageous in the context of the present invention if the oily phase of the O/W emulsion contains one or more oil components chosen from the group of the compounds butylene glycol dicaprylate/dicaprate, myristyl myristate, octyldodecanol, C12-15 alkyl benzoate caprylic/capric triglyceride, diisopropyl sebacate, dicaprylyl ether, mineral oil, silicone oil.

It is advantageous according to the invention if the formulation according to the invention contains one or more preservatives, in particular one or more parabens and/or phenoxyethanol.

The O/W emulsion according to the invention can moreover contain further cosmetic active ingredients, auxiliary substances and additives, for example EDTA and perfume substances, such as limonene, linalool, benzyl benzoate, hydroxyisohexyl 3-cyclohexene, carboxaldehyde, hexyl cinnamal, benzyl salicylate, eugenol, butylphenyl methylpropional, alpha-isomethyl ionone, citronellol, coumarin, geraniol, cinnamyl alcohol, citral.

Sensorial additives can furthermore in the emulsion, such as distarch phosphate, sodium starch octenylsuccinate, aluminum starch octenylsuccinate, acrylonitrile/methacrylonitrile/methyl methacrylate copolymer+isopentane+magnesium hydroxide, tapioca starch, silica, nylon 6 polyamide 5, micronized talk.

The preparation process according to the invention and the product prepared by the preparation process are characterized according to the invention as advantageous according to the invention by the following details:

It is thus advantageous according to the invention if the emulsifier(s) has/have been added to the oily phase before this is added to the aqueous phase.

According to the invention, the hot aqueous phase advantageously has a temperature of from 50 to 95° C., preferably a temperature of from 75 to 90° C. and particularly preferably a temperature of about 85° C. The term "about" in this context is intended solely to characterize the slight temperature variations typical of such processes.

According to the invention, the heated oily phase advantageously has a temperature of from 50 to 95° C., preferably a temperature of from 75 to 90° C. and particularly preferably a temperature of about 85° C. The term "about" in this context is intended solely to characterize the slight temperature variations typical of such processes.

Mixers from Becomix or Krieger are advantageously used according to the invention as homogenizers.

According to the invention, the homogenization is advantageously carried out over a period of time of from 2 to 25 minutes.

According to the invention, the stirring speed during the homogenization is advantageously from 500 to 2,000 rpm, a stirring speed of from 1,000 to 1,400 rpm being preferred according to the invention, and a stirring speed of 1,200 rpm (+−50 rpm) being particularly preferred according to the invention.

In process step d), according to the invention the formulation is advantageously cooled to a temperature of from 25 to 40° C., a temperature of about 35° C. being preferred. The term "about" in this context is intended solely to characterize the slight temperature variations typical of such processes.

The perfume substances and preservatives are preferably mixed with one another before the addition to the emulsion.

The perfume substances and preservatives are preferably dissolved in ethanol before the addition to the emulsion.

The addition of the perfume substances and preservatives is advantageously carried out according to the invention at a temperature of below 30° C.

Advantageously, in the context of the present invention the formulations can serve for care of the skin, cosmetic protection from light or as a make-up product in decorative cosmetics.

According to their make-up, cosmetic compositions in the context of the present invention can be used, for example, as skin protection cream, day or night cream etc. It may be possible and advantageous to use the compositions according to the invention as a base for pharmaceutical formulations.

According to the invention, the formulation according to the invention is used in particular for protection from ageing of the skin (in particular for protection from ageing of the skin of UV origin) and as a sunscreen composition.

According to the invention, the formulation according to the invention advantageously has a pH of from 5 to 8. This can be established by conventional acids, bases and buffer systems.

Comparison Experiments

It was possible to demonstrate the inventive effect with the following comparison experiments:

The following recipes were prepared and the content of licorice extract (containing licochalcone A) was determined before and after storage for 4 weeks in an incubating cabinet at 40° C.

Recipe sample 1 contains a preparation without the stabilizers butyl methoxydibenzoyl methane and octocrylene. Recipe sample 2 additionally contains the two stabilizers.

| INCI name(s) | Sample 1 m [%] | Sample 2 m [%] |
|---|---|---|
| Alcohol denat. | 6.00 | 6.00 |
| Sodium hydroxide | 0.60 | 0.60 |
| Cetearyl alcohol + PEG-40 castor oil + sodium cetearyl sulfate | 2.00 | 2.00 |
| Glyceryl stearate SE | 0.80 | 0.80 |
| Trisodium EDTA | 1.00 | 1.00 |
| Methylparaben | 0.30 | 0.30 |
| Phenoxyethanol | 0.20 | 0.20 |
| Bis-ethylhexyloxyphenol methoxyphenol triazine | 3.50 | 3.50 |
| Butyl methoxydibenzoyl methane | | 4.50 |
| Diethylhexyl butamido triazone | 1.00 | 1.00 |
| Ethylhexyl methoxycinnamate + BHT | 2.00 | 2.00 |
| Octocrylene | | 4.50 |
| Phenylbenzimidazole sulfonic acid | 2.00 | 2.00 |
| Glycerin | 2.00 | 2.00 |
| Butylene glycol dicaprylate/dicaprate | 7.00 | 7.00 |
| C12-15 alkyl benzoate | 11.00 | 11.00 |
| Myristyl myristate | 2.00 | 2.00 |
| Octyldodecanol | 5.50 | 5.50 |
| *Glycyrrhiza inflata* root extract (licochalcone A) | 0.025 | 0.025 |
| Titanium dioxide + trimethoxycaprylylsilane | 4.00 | 4.00 |
| Acrylates/C10-30 alkyl acrylate cross polymer | 0.05 | 0.05 |
| Cetyl alcohol | 2.50 | 2.50 |
| Tapioca starch | 1.00 | 1.00 |
| Xanthan gum | 0.80 | 0.80 |
| Tocopheryl acetate | 0.50 | 0.50 |
| Water | to 100.000 | to 100.000 |

Experimental Design

Determination of the licorice content (licochalcone A) of the test sample after 4 weeks storage stability at 40° C. incubating cabinet storage.

Method Employed:

The licorice content was determined by means of HPLC-DAD via an external calibration series. The licorice provided by the client was employed for the calibration, NART: 96146-90000-00, batch 17743901. The contents stated in the report are based on the reference substance employed for the calibration.

Results:

| Sample designation | Content in % | |
|---|---|---|
| | actual | theoretical |
| Sample 1 | <0.005 | 0.025 |
| Sample 2 | 0.018 | 0.025 |

CONCLUSION

The specimen sample 2 contains more licorice extract (licochalcone A) than the specimen sample 1. The addition of the stabilizers butyl methoxydibenzoyl methane and octocrylene leads to an increased heat and storage stability of the licorice extract (licochalcone A).

EXAMPLES

The following examples are intended to illustrate the present invention without limiting it. Unless stated otherwise, all the amounts data, contents and percentage contents are based on the weight and the total amount or on the total weight of the formulations.

| INCI name(s) | 1 m [%] | 2 m [%] | 3 m [%] | 4 m [%] |
|---|---|---|---|---|
| Acrylonitrile/methacrylonitrile/methyl methacrylate copolymer + isopentane + magnesium hydroxide | 0.30 | | 0.10 | |
| Tapioca starch | | 0.50 | | 1.00 |
| Sodium starch octenylsuccinate | | 0.30 | 0.80 | |
| Polyamide 5 | | | | 0.50 |
| Distarch phosphate | | | 0.80 | |
| Aluminum starch octenylsuccinate | | 0.50 | | |
| Alcohol denat. | 8.00 | 7.00 | 8.00 | 5.00 |
| Dicaprylyl ether | | | 1.00 | 2.00 |
| Caprylic/capric triglyceride | 2.00 | | | 1.00 |
| Diisopropyl sebacate | | 4.00 | 5.00 | |
| C12-15 alkyl benzoate | 8.00 | 2.00 | | 6.50 |
| Cetearyl alcohol + PEG-40 castor oil + sodium cetearyl sulfate | 2.00 | 1.00 | 2.50 | 1.00 |
| Cetyl alcohol | 1.00 | | 2.20 | 1.50 |
| Ethylhexyl salicylate | 4.50 | | 2.00 | 1.00 |
| Bis-ethylhexyloxyphenol methoxyphenyl triazine | 2.30 | 1.00 | 2.50 | 1.50 |
| Butyl methoxydibenzoyl methane | 4.50 | 5.00 | 2.00 | 4.50 |
| Phenylbenzimidazole sulfonic acid | 2.50 | 1.00 | 4.00 | 2.00 |
| Diethylamino hydroxybenzoyl hexyl benzoate | 2.00 | | 4.00 | |
| Octocrylene | 5.00 | 9.00 | 7.00 | 4.50 |
| Diethylhexyl butamido triazone | | 1.00 | | 1.50 |
| Glycerin | 5.00 | 2.00 | 0.90 | 8.00 |
| Glyceryl stearate SE | 0.50 | 1.00 | 0.50 | 0.65 |
| *Glycyrrhiza inflata* root extract | 0.10 | 0.01 | 0.02 | 0.03 |
| Methylparaben | 0.30 | 0.20 | 0.20 | |
| Myristyl myristate | 1.00 | 1.50 | 3.00 | 1.50 |
| Octyldodecanol | 5.50 | 4.00 | 2.00 | |
| Phenoxyethanol | 0.20 | 0.10 | 0.20 | 0.20 |
| Titanium dioxide + trimethoxycaprylylsilane | 2.00 | 3.00 | 1.50 | 5.00 |
| Tocopheryl acetate | 0.50 | 0.50 | 0.10 | 0.50 |
| Perfume | q.s. | q.s. | q.s. | q.s. |
| Sodium hydroxide | q.s. | q.s. | q.s. | q.s. |
| Trisodium EDTA | q.s | q.s. | q.s. | q.s. |
| Xanthan gum | 0.40 | 0.40 | 0.40 | 0.40 |
| Water | to 100.00 | to 100.00 | to 100.00 | to 100.00 |

| INCI name(s) | 5 m [%] | 6 m [%] | 7 m [%] | 8 m [%] | 9 m [%] |
|---|---|---|---|---|---|
| Acrylonitrile/methacrylonitrile/methyl methacrylate copolymer + isopentane + magnesium hydroxide | 0.30 | | 0.10 | | |
| Tapioca starch | | 0.50 | | 1.00 | 1.00 |
| Sodium starch octenylsuccinate | | 0.30 | 0.80 | | |
| Polyamide 5 | | | | 0.50 | 0.50 |
| Distarch phosphate | | | 0.80 | | |
| Aluminum starch octenylsuccinate | | 0.50 | | | |
| Potassium cetyl phosphate | 2.00 | | | | |
| Sodium stearoyl glutamate | | 2.50 | | | |
| Sucrose polystearate + hydrogenated polyisobutene | | 0.50 | | | |
| Polyglyceryl-3 methylglucose distearate | | | 5.00 | | |
| Triceteareth-4 phosphate | | | | 2.00 | |
| Stearic acid | | | | | 2.50 |

-continued

| | | | | | |
|---|---|---|---|---|---|
| Alcohol denat. | 8.00 | 7.00 | 8.00 | 5.00 | 5.00 |
| Dicaprylyl ether | | | 1.00 | 2.00 | 2.00 |
| Caprylic/capric triglyceride | 2.00 | | | 1.00 | 1.00 |
| Diisopropyl sebacate | | 4.00 | 5.00 | | |
| C12-15 alkyl benzoate | 8.00 | 2.00 | | 6.50 | 6.50 |
| Cetyl alcohol | 1.00 | | 2.20 | 1.50 | 1.50 |
| Ethylhexyl salicylate | 4.50 | | 2.00 | 1.00 | 1.00 |
| Bis-ethylhexyloxyphenol methoxyphenyl triazine | 2.30 | 1.00 | 2.50 | 1.50 | 1.50 |
| Butyl methoxydibenzoyl methane | 4.50 | 5.00 | 2.00 | 4.50 | 4.50 |
| Phenylbenzimidazole sulfonic acid | 2.50 | 1.00 | 4.00 | 2.00 | 2.00 |
| Diethylamino hydroxybenzoyl hexyl benzoate | 2.00 | | 4.00 | | |
| Octocrylene | 5.00 | 9.00 | 7.00 | 4.50 | 4.50 |
| Diethylhexyl butamido triazone | | 1.00 | | 1.50 | 1.50 |
| Glycerin | 5.00 | 2.00 | 0.90 | 8.00 | 8.00 |
| *Glycyrrhiza inflata* root extract | 0.10 | 0.01 | 0.02 | 0.03 | 0.03 |
| Methylparaben | 0.30 | 0.20 | 0.20 | | |
| Myristyl myristate | 1.00 | 1.50 | 3.00 | 1.50 | 1.50 |
| Octyldodecanol | 5.50 | 4.00 | 2.00 | | |
| Phenoxyethanol | 0.20 | 0.10 | 0.20 | 0.20 | 0.20 |
| Titanium dioxide + trimethoxycaprylylsilane | 2.00 | 3.00 | 1.50 | 5.00 | 5.00 |
| Tocopheryl acetate | 0.50 | 0.50 | 0.10 | 0.50 | 0.50 |
| Perfume | q.s. | q.s. | q.s. | q.s. | q.s. |
| Sodium hydroxide | q.s. | q.s. | q.s. | q.s. | q.s. |
| Trisodium EDTA | q.s. | q.s. | q.s. | q.s. | q.s. |
| Xanthan gum | 0.40 | 0.40 | 0.40 | 0.40 | 0.40 |
| Water | to 100.00 | to 100.00 | to 100.00 | to 100.00 | to 100.00 |

What is claimed is:

1. A process for the preparation of a cosmetic O/W emulsion, wherein the process consists of
   (i) adding a heated oil phase comprising 2-ethylhexyl 2-cyano-3,3-diphenylacrylate, 4-(tert-butyl)-4'-methoxydibenzoylmethane and, optionally, one or more further oil-soluble UV filters to a hot aqueous phase,
   (ii) homogenizing the oil and water phases to obtain an O/W emulsion,
   (iii) externally cooling the emulsion, and
   (iv) adding at least one of licorice extract dissolved in ethanol and licochalcone A dissolved in ethanol to the cooled emulsion with stirring.

* * * * *